United States Patent [19]

Voelskow et al.

[11] Patent Number: 4,567,140
[45] Date of Patent: Jan. 28, 1986

[54] MICROBIAL POLYSACCHARIDES, PROCESS FOR THEIR PREPARATION, MICROORGANISMS SUITABLE FOR THIS AND USE OF THE POLYSACCHARIDES

[75] Inventors: Hartmut Voelskow, Hattersheim am Main; Merten Schlingmann, Königstein, both of Fed. Rep. of Germany

[73] Assignee: Hoechst Aktiengesellschaft, Frankfurt am Main, Fed. Rep. of Germany

[21] Appl. No.: 487,019

[22] Filed: Apr. 21, 1983

[30] Foreign Application Priority Data

Apr. 22, 1982 [DE] Fed. Rep. of Germany ....... 3214953

[51] Int. Cl.$^4$ ...................... C12P 39/00; C12P 19/12; C08B 37/00; B01J 13/00; C12R 1/01; C12R 1/38
[52] U.S. Cl. ...................... 435/42; 435/101; 435/104; 435/253; 435/822; 435/874; 536/114; 536/123; 252/315.3

[58] Field of Search .......... 435/101, 104, 42; 536/114, 123; 252/315.3

[56] References Cited

U.S. PATENT DOCUMENTS 4,304,906 12/1981 Kang et al. .......................... 536/114
4,329,448 5/1982 Cox et al. ............................ 536/123

OTHER PUBLICATIONS

American Type Culture Collection, Catalogue of Strains, 15th Edition, 1982, pp. 65, 66, and 175.

Primary Examiner—Lionel M. Shapiro
Attorney, Agent, or Firm—Finnegan, Henderson, Farabow, Garrett & Dunner

[57] ABSTRACT

Polysaccharides are obtained by fermentation using a mixed culture of several microorganisms, of which at least one also produces a polysaccharide in pure culture, which polysaccharides are suitable as viscosity regulators. A mixed culture of the strains *Pseudomonas maltophilia* DSM 2130 and *Agrobacterium tumefaciens* DSM 2128 is particularly suitable.

15 Claims, No Drawings

MICROBIAL POLYSACCHARIDES, PROCESS FOR THEIR PREPARATION, MICROORGANISMS SUITABLE FOR THIS AND USE OF THE POLYSACCHARIDES

Microbial polysaccharides, such as xanthan gum are used widely as viscosity regulators, such as, for example, in crude oil production, as an additive to plastics dispersions and for colorant formulations.

The invention relates to extracellular polysaccharides which can be obtained by fermentation using a mixed culture of several microorganisms, of which at least one also produces a polysaccharide in pure culture, and a process for the preparation of polysaccharides by fermentation using microorganisms, which comprises employing a mixed culture of several microorganisms, of which at least one also produces a polysaccharide in pure culture; particularly suitable microorganisms for this purpose and the use of the polysaccharides which can thus be obtained as viscosity regulators for liquid, particularly aqueous, systems. Preferred embodiments of the invention are illustrated in more detail in the following text.

Depending on the microorganisms employed, the mixed cultures can be inoculated immediately after mixing into the production medium or are initially maintained as mixed cultures over some generations before being introduced into the production medium. The procedure which is advantageous in the particular case can easily be found by means of preliminary experiments.

The optimal medium for the mixed culture can differ from the optimal media for the pure cultures. The most advantageous media can again be discovered by the expert by means of simple preliminary experiments, without inventive effort.

Compared to the polysaccharides which are produced by the pure cultures employed in each case, the biopolymers according to the invention are distinguished by improved properties. Thus, they exhibit, in aqueous and/or aqueous salt-containing solution, a viscosity which is markedly above that obtained with equal amounts of the polysaccharides which have been obtained with the corresponding pure cultures. Appropriate viscosity measurements on the solutions of the products can also be employed as a criterion for the selection of the culture media.

Species of the following genera of bacteria or fungi can be used for the mixed cultures to be employed according to the invention: Agrobacterium, Alcaligenes, Arthrobacter, Aureobasidium, Azotobacter, Bacillus, Corynebacterium, Erwinia, Hansenula, Klebsiella, Leuconostoc, Methylococcus, Methylocystis, Methylomonas, Nocardia, Pseudomonas, Sclerotium, Streptomyces and Xanthomonas.

The (volume) ratio of the pure cultures employed for the mixed culture can be from 1:1 to 1:10,000 and is preferably in the range from 1:1 to 1:100, in particular from 1:1 to 1:10.

The mixed culture preferably contains a pure culture of the genus Pseudomonas, in particular the strain *Pseudomonas maltophilia* which is deposited in the German Collection of Microorganisms under Number DSM 2130. The invention furthermore relates to this strain, together with its mutants and variants which likewise form extracellular polymers with advantageous properties in mixed cultures.

Since many cultures of Pseudomonas alone do not form utilizable polymers and, in some cases, only form small amounts of low viscosity mucilages, it is surprising that mixed cultures containing strains of this type produce polymers with outstanding properties. On using Pseudomonas cultures, mixed cultures are frequently obtained which are stable over a large number of generations. The output of the polymers with improved rheological properties according to the invention frequently occurs only after a certain time of adaptation of the mixed culture.

Particularly suitable species of bacteria as components for mixed cultures with Pseudomonas species, in particular *Pseudomonas maltophilia*, are the following: *Agrobacterium tumefaciens, Agrobacterium radiobacter, Agrobacterium rhizogenes, Agrobacterium rubi, Klebsiella pneumoniae, Klebsiella planticola,* Enterobacter sp., Xanthomonas sp. and *Bacillus polymyxa*. "Enterobacter sp." and "Xanthomonas sp." in this context represent all species of these genera which are known as polysaccharide-forming bacteria.

Using the following bacterial strains mixed with *Pseudomonas maltophilia* DSM 2130, biopolymers were obtained which exhibit a particularly marked increase in viscosity compared to the product of the pure culture:

| Bacterium | Increase in viscosity |
| --- | --- |
| *Enterobacter sakazaki* | 30% |
| *Bacillus polymyxa* | 40% |
| *Klebsiella pneumoniae* | 45% |
| *Agrobacterium tumefaciens* | 100% |

*Agrobacterium tumefaciens*, which is deposited in the German Collection of Mcroorganisms under number DSM 2128, is particularly perferred for a mixed culture with *Pseudomonas maltophilia* DSM 2130. The invention furthermore relates to the former strain, together with its mutants and variants which likewise form extracellular polymers with advantageous properties in mixed cultures. The corresponding mixed cultures can be maintained stable for at least 3 months in a continuous culture.

Fermentation is carried out in a manner known per se. The fermentation medium contains as the carbon source monomeric, dimeric or oligomeric sugars, such as, for example, glucose, sucrose or lactose or any desired mixture of these sugars, the concentration of sugar in the medium being 10 to 100 g/liter, preferably 40 to 60 g/liter. In an industrially particularly advantageous manner, in place of the pure sugars, carbohydrate-containing raw materials are employed, for example, liquid sugar, molasses, whey or whey powder, the sugar concentration corresponding to the values mentioned above.

Suitable sources of nitrogen in the fermentation medium are organic products, such as soybean flour, corn-steep (water from corn swelling), yeast extract, wheat bran and urea or inorganic salts, such as nitrates or any ammonium salts or any mixtures of two or more of the substrates mentioned, the concentration of nitrogen in the medium being selected so that it corresponds to 0.5 to 250 mM, preferably 10 to 50 mM, as $NH_3$.

In the fermentation, the pH is maintained in the range from 5 to 9, preferably 6 to 7.5.

The temperature during the growing phase is maintained at about 35° to 45° C. for about 8 to 12 hours and then between about 15° and 45° C., preferably 20° to 40°

C., in particular 25° to 35° C., until the end of polymer formation. The sugar substrate and the nitrogen source are either added in the total amount right at the start of fermentation or are gradually metered into the fermenter. In the latter case, the sugar concentration is advantageously maintained constant between 0.001 to 1% by weight over the entire course of fermentation and the nitrogen source is metered in so that a constant concentration between 0.0001 and 1 mM $NH_3$ prevails in the medium during fermentation.

The extracellular polymer can be isolated from the fermentation medium by ultrafiltration and/or precipitation, for example with polar solvents, such as acetone or lower alkanols or with salts, such as magnesium chloride or calcium chloride and bases such as sodium hydroxide or potassium hydroxide. Before precipitating out, the product can be treated, for clarification and protein cleavage, with cell-lysing enzymes, such as lysozyme, or with proteolytic enzymes, such as trypsin, or with the two consecutively, by which means a particularly pure product is obtained. Before precipitating the polymer, it is also possible to add to the fermentation solution reagents which precipitate out protein and nucleic acids, the solution subsequently being separated off from the materials which have precipitated out, for example by filtration or centrifugation.

The fermentation and the isolation of the product can each be carried out discontinuously or continuously.

Preferred polymers according to the invention have the following compositions: glucose and galactose in a molar ratio of about 4:1 to 8:1 as the main components and about 4 to 9% by weight of pyruvate, about 5 to 15% by weight of succinate, about 0.5 to 7% by weight of rhamnose and about 0.2 to 5% by weight of mannose as subsidiary components.

The invention is illustrated in more detail in the following examples. Percentage data and ratios relate to weight unless otherwise specified.

EXAMPLE 1

Preparation of the mixed culture

The strains DSM 2128 and 2130 are initially cultured separately on the following media: 30 g of glucose, 3 g of cornsteep (dry), 0.5 g of $MgSO_4.7\ H_2O$, 1 g of $KH_2PO_4$ and 5 g of $CaCO_3$ for strain DSM 2130 and, additionally, 1 g of $NaNO_3$ for strain 2128, with tap water ad 1 liter in each case. For agar cultures, 1.8% of agar is added to the media. The incubation time for agar cultures is 2 days at 30° C. Shaking cultures are carried out in 300 ml flasks each containing 100 ml of mixture at 30° C. on a circular shaker (amplitude 5 cm, speed 180 rpm), incubation time 24 hours.

Before inoculating a fermenter culture, the cultures of the two strains are mixed 1:1 and inoculated into the medium containing $NaNO_3$ mentioned. The prepared mixed culture is again inoculated 2 to 3 times in the same medium after a growth period of 24 hours in each case and is thus stabilized. The ratio of mixing of the two species does not change subsequently on further reinoculation and remains stable, with regular reinoculation, for at least 2 years.

Fermentation 300 to 500 ml of the stabilized mixed culture described above are used as inoculum for a fermenter of volume 10 liters which contains a fermentation medium of the following composition (per liter):

| | |
|---|---|
| 45 g of glucose | trace element solution: |
| 1.5 g of $NaNO_3$ | per liter |
| 0.5 g of $(NH_4)_2HPO_4$ | 3 g of $CaCl_2$ |
| 2 g of $KH_2PO_4$ | 1 g of Fe(III) citrate |
| 1 g of $Na_2HPO_4.7H_2O$ | 0.2 g of $MnSO_4$ |
| 0.5 g of $MgSO_4.7H_2O$ | 0.1 g of $ZnCl_2$ |
| 0.5 g of yeast extract | 0.025 g of $CuSO_4$ |
| 5 ml of trace element solution | 0.022 g of $CoCl_2$ |
| | 0.025 g of $Na_2MoO_4.2H_2O$ |
| | 0.010 g of ethylene- |
| | diaminetetraacetic acid. |

Fermentation is carried out at 30° C., the contents being stirred with a spiral stirrer (450 rpm). The aeration at the start is 10 liter/min and the amount of air is increased up to 18 liter/min with increasing viscosity after about 24 hours. The pH is adjusted to 6.8 with hydrochloric acid and sodium hydroxide solution. After 48 to 60 hours, the glucose has been entirely degraded, 25 g of polymer being formed per liter of fermentation solution.

The culture solution is pasteurized before workup by heating to 85° C. and, after dilution, the bacterial cells are centrifuged off. Subsequently, the polymer is precipitated out by addition of acetone, about 1.5 times the volume of the aqueous solution having been necessary. The precipitated product is dried; it still contains about 5% of protein.

In place of centrifugation, the bacterial cells can be broken down chemically or enzymatically in the fermentation solution by known processes. The precipitation can also be carried out with ispropanol or another lower water-soluble alkanol instead of acetone.

When a purer product is desired, the proteins and nucleic acids can initially be precipitated out and separated off in a known manner and the polysaccharide then precipitated out, again dissolved in water and finally precipitated.

The following table shows the viscosity of the product thus obtained compared to xanthan gum at a sheer gradient D=10/sec and D=424/sec in aqueous and salt-containing solution (13% $NaCl+1\%$ $CaCl_2$), at a concentration of 0.2% (data in mPa.s, at 22° C.):

| Sheer gradient $D (s^{-1})$ | Product Xanthan in water | | Product Xanthan in salt solution | |
|---|---|---|---|---|
| 10 | 265 | 118.7 | 256 | 118.6 |
| 424 | 21 | 11 | 16.5 | 13 |

The polysaccharide solution is composed of the following monomers: glucose and galactose in the ratio of 6:1 to 7:1 as main components, 5.1 to 7.9% of pyruvate, 6.4 to 8.7% of succinate, 1 to 1.5% of rhamnose and about 0.4% of mannose as subsidiary components.

Elemental analysis gave: 41% C, 5.6% H, 45% O, 1.7% N, 0.8% P.

EXAMPLE 2

Fermentation is carried out as described in Example 1. However, after pasteurization, the product is precipitated out as follows:

64 g of magnesium chloride per 100 g of polymer are added and dissolved. The solution is then made alkaline with 51 g of sodium hydroxide, the magnesium salt of the polymer precipitating out. The precipitated product is filtered off and washed with a mixture of 2 parts by volume of isopropanol and 1 part by volume of 4 M hydrochloric acid, 15 liters being used per kg of precipitation product. The product is subsequently washed with the same amount of isopropanol and, having been freed of magnesium ions, is then dried.

It is also possible to employ 75 g of calcium chloride in place of the 64 g of magnesium chloride, the calcium salt of the polymer then being precipitated off.

Further purification can be carried out as indicated in Example 1.

EXAMPLE 3

For continuous fermentation, the same medium is used as in Example 1. After a growth period of 20 hours, continuous metering in of the same medium is started. The rate of dilution is 0.04 per hour. The same amount is continuously removed and transferred to work-up. All the steps of work-up described in Example 1 are now carried out continuously, but the pasteurization of the solutionn after removal from the fermenter is omitted. 90% of the quantity of cells which have been centrifuged off is returned to the fermenter and 10% is pasteurized and discarded. The suspension removed from the fermenter contains 20-22 g of polymer product per liter and a residual sugar content below 0.5%. The mixture of bacterial strains remains stable for at least 3 months without adjustment measures.

Annex: Protocol of Results (by DSM - Deutsche Sammlung von Mikroorganismen, Grisebachstr. 8, 3400 Gottingen, Federal Republic of Germany)

|  | DSM 2128 | DSM 2130 |
|---|---|---|
| Cell form | rods | — |
| Length μm | 1.2-2 | 1-2 |
| Width μm | 0.5-0.8 | 0.4-0.6 |
| Mobility | + | + |
| Flagellae | 1-3 peritrich | polar, multitrich |
| Gram reaction | — | — |
| Spores | — | — |
| Formation of poly-β-hydroxybutyrate | — | — |
| Oxidase | + | — |
| Catalase | + | + |
| Growth |  |  |
| anaerobe | — | — |
|  | +, 37° C. | +, 42° C. |
| pH 5.6 | + | + |
| pH 4.5 | — | + |
| Mac-Conkey-Agar | + | + |
| SS-Agar | — | — |
| Centrimid-Agar | — | + |
| Pigment formation |  |  |
| no diffusion | — | yellow |
| diffusion | — | — |
| fluorescent | — | — |
| Acid formation from |  |  |
| Glucose aerobe | + | — |
| anaerobe | — | — |
| Fructose aerobe | + | — |
| Maltose | + | + |
| Gas formation from |  |  |
| Glucose | — | — |
| ONPG | + | + |
| Arginine dihydrolase | — | — |
| Lysine decarboxylase | — | + |
| Ornithine decarboxylase | — | — |
| H₂S (lead acetate) | + | — |
| Voges-Proskauer | — | — |
| Phenylalanine deaminase |  |  |
| Indole | — | — |
| Nitrite from nitrate | + | + |
| Denitrification | — | — |
| Lecithinase | — | — |
| Urease | + | — |
| Degradation of |  |  |
| Starch | — | — |

Annex: Protocol of Results (by DSM - Deutsche Sammlung von Mikroorganismen, Grisebachstr. 8, 3400 Gottingen, Federal Republic of Germany)

|  | DSM 2128 | DSM 2130 |
|---|---|---|
| Gelatine | — | + |
| Caseine | — | + |
| Tyrosine | — | + |
| Tween 80 | — | + |
| DNA | — | + |
| Esculine | + | + |
| Poly-β-hydroxybutyrate | — | — |
| Acetamide | — |  |
| Need of growth factor |  | methionine |
| Substrate Degradation |  |  |
| Acetate | + | + |
| Citrate | — |  |
| Methanol | — |  |
| Glucose | + |  |
| β-hydroxybutyrate |  | — |
| Formation of 3-ketolactose | + |  |
| Result | Pseudomonas maltophilia | Agrobacterium tumefaciens |

We claim:

1. Extracellular polysaccharides containing glucose and galactose in a molar ratio of about 4:1 to about 8:1 as the main components and about 4 to about 9% by weight of pyruvate, about 5 to about 15% by weight of succinate, about 0.5 to about 7% by weight of rhamnose and about 0.2 to about 5% by weight of mannose as subsidiary components obtained by fermentation using a mixed culture of more than one microorganism of which at least one microorganism is capable of producing a polysaccharide in pure culture.

2. A process for the preparation of polysaccharides as claimed in claim 1 by fermentation which comprises employing a mixed culture of more than one microorganism of which at least one also produces an exopolysaccharide in pure culture.

3. The process as claimed in claim 2, wherein one of the microorganisms is the strain *Pseudomonas maltophilia* DSM 2130.

4. The process as claimed in claim 2, wherein one of the microorganisms is the strain *Agrobacterium tumefaciens* DSM 2128.

5. The process as claimed in claim 3, wherein one of the microorganisms is the strain *Agrobacterium tumefaciens* DSM 2128.

6. The process as claimed in claim 2, wherein the polymer formed is isolated from the fermentation medium by ultrafiltration and/or precipitation.

7. A substantially pure culture of *Paeudomonas maltophilia* DSM 2130 capable of producing extracellular polysaccharides.

8. A substantially pure culture of *Agrobacterium tumefaciens* DSM2128 capable of producing extracellular polysacchrides.

9. An essentially biologically pure culture of the 30 strain claimed in claim 7.

10. Mutants and variants of the strain claimed in claim 7, capable of producing in a mixed culture extracellular polysaccharides containing glucose and galactose in a molar ratio of about 4:1 to 8:1 as the main components and about 4 to 9% by weight of pyruvate, about 5 to 15% by weight of succinate, about 0.5 to 7% by weight of rhamnose and about 0.2 to 5% by weight of mannose as subsidiary components.

11. An essentially biologically pure culture of the strain claimed in claim 8.

12. Mutants and variants of the strain claimed in claim 8 capable of producing in a mixed culture extracellular polysaccharides containing glucose and galactose in a molar ratio of about 4:1 to 8:1 as the main components and about 4 to 9% by weight of pyruvate, about 5 15% by weight of succinate, about 0.5 to 7% by weight of rhamnose and about 0.2 to 5% by weight of mannose as subsidiary components.

13. A mixed culture of *Pseudomonas maltophilia* DSM2130 and *Agrobacterium tumefaciens* DSM2128.

14. A process for regulating the viscosity of liquid systems which comprises adding to the system a polysaccharide as claimed in claim 1.

15. The process as claimed in claim 14, wherein the liquid system is an aqueous system.

* * * * *

UNITED STATES PATENT AND TRADEMARK OFFICE
CERTIFICATE OF CORRECTION

PATENT NO. : 4,567,140
DATED : January 28, 1986
INVENTOR(S) : VOELSKOW et al.

It is certified that error appears in the above—identified patent and that said Letters Patent is hereby corrected as shown below:

Claim 7, line 1, Paeudomonas should be --Pseudomonas--.

Claim 8, line 2, DSM2128 should be --DSM 2128--.

Signed and Sealed this

Twenty-ninth Day of April 1986

[SEAL]

Attest:

DONALD J. QUIGG

Attesting Officer

Commissioner of Patents and Trademarks